United States Patent [19]

Thompson

[11] Patent Number: 5,056,128
[45] Date of Patent: Oct. 8, 1991

[54] X-RAY FILTRATION APPARATUS

[76] Inventor: George Thompson, 118, 7930 Bowness Road N.W., Calgary, Alberta, Canada, T3B 0H3

[21] Appl. No.: 509,637

[22] Filed: Apr. 17, 1990

[30] Foreign Application Priority Data

Apr. 17, 1989 [CA] Canada .................................. 596939

[51] Int. Cl.$^5$ .............................................. G21K 3/00
[52] U.S. Cl. .................... 378/156; 378/158; 378/145
[58] Field of Search ............... 378/147, 150, 151, 156, 378/159, 157, 148, 145, 158

[56] References Cited

U.S. PATENT DOCUMENTS

| 3,678,233 | 7/1972 | Faw et al. | 378/158 |
| 4,198,570 | 4/1980 | McHugh et al. | 378/158 |
| 4,214,167 | 7/1980 | Gäde | 378/158 |
| 4,266,139 | 5/1981 | Sportelli et al. | 378/147 |
| 4,707,846 | 11/1987 | Sportelli et al. | 378/147 |

Primary Examiner—Edward P. Westin
Assistant Examiner—Kim-Kwok Chu
Attorney, Agent, or Firm—George Haining Dunsmuir

[57] ABSTRACT

In general, it can be difficult and time consuming to mount X-ray shields or filters on an X-ray machine. An even more serious difficulty is that of effectively masking all but a specific area. A relatively effective X-ray shielding support, which can be adjusted in any direction to mask all but a specific area includes an apertured base plate for mounting on the machine to define a frame around the collimator aperture of the machine, a variety of spacers for mounting on the base plate, and filter holders for mounting on at least one of the base plate and spacers. The spacers and filter holders are magnetic to make interconnection of the elements quick and easy.

6 Claims, 4 Drawing Sheets

X-RAY FILTRATION APPARATUS

BACKGROUND OF THE INVENTION

1. Field of Invention

This invention relates to an X-ray shielding support device.

2. Discussion of the Prior Art

In spite of considerable development in X-ray taking techniques, a need still exists for effective shielding, inter alia, to compensate for variations in the thickness, density and the absorption properties of the object being studied. By appropriate shielding, the X-ray image produced is of sufficient detail, contrast and intensity over its entire area to constitute a useful diagnostic aid. It is also desirable to subject the patient to the smallest possible X-ray dosage.

Examples of X-ray shields or filters are found in Canadian Patents Nos. 929,285, issued to P. Edholm et al on June 26, 1973 and 1,147,069, issued to P. Charrier on May 24, 1983, and U.S. Pat. Nos. 2,426,884, issued to J. Kieffer on Sept. 2, 1947; 3,232,248 issued to F. L. Bushnell on Feb. 8, 1966; 3,631,249, issued to M. Friede et al on Dec. 28, 1971; 3,678,233 issued to F. L. Faw et al on July 18, 1972; 3,937,971, issued to R. A. Morrison et al on Feb. 10, 1976; 3,944,838, issued to E. A. Gade on Mar. 6, 1976; 3,986,036, issued to J. W. Harper et al on Oct. 12, 1976; 4,082,957, issued to A. F. Morlan on Apr. 4, 1978; 4,214,167, issued to E. A. Gade on July 22, 1980; 4,255,667, issued to L. E. Bolin et al on Mar. 10, 1981, and U.S. Pat. No. 4,266,139, issued to L. Sportelli et al on May 5, 1981. While the patented devices offer worthwhile solutions to the problem of X-ray shielding, in general the shields are unduly restricted and rigid.

The object of the present invention is to overcome the disadvantages of existing X-ray shielding structures by providing an X-ray shielding support device which facilitates the tailoring of an X-ray beam in terms of area and intensity.

GENERAL DESCRIPTION OF INVENTION

Accordingly, the present invention relates to an X-ray shielding support device comprising apertured, metal base plate means for defining a frame around the collimator aperture of an X-ray machine; metal spacer means for mounting on said base plate means to define a support surface around and spaced from the collimator aperture and base plate means; and X-ray filter holder means for mounting on at least one of said base plate means and said spacer means, selective of said base plate means, spacer means and filter holder means being magnetic, whereby the holder means can be mounted on said base plate means or on said spacer means to shield any area in front of the collimator aperture.

BRIEF DESCRIPTION OF DRAWINGS

The invention will be described in greater detail with reference to the accompanying drawings, which illustrate a preferred embodiment of the invention and wherein.

DESCRIPTION OF PREFERRED EMBODIMENTS

Figure 1:
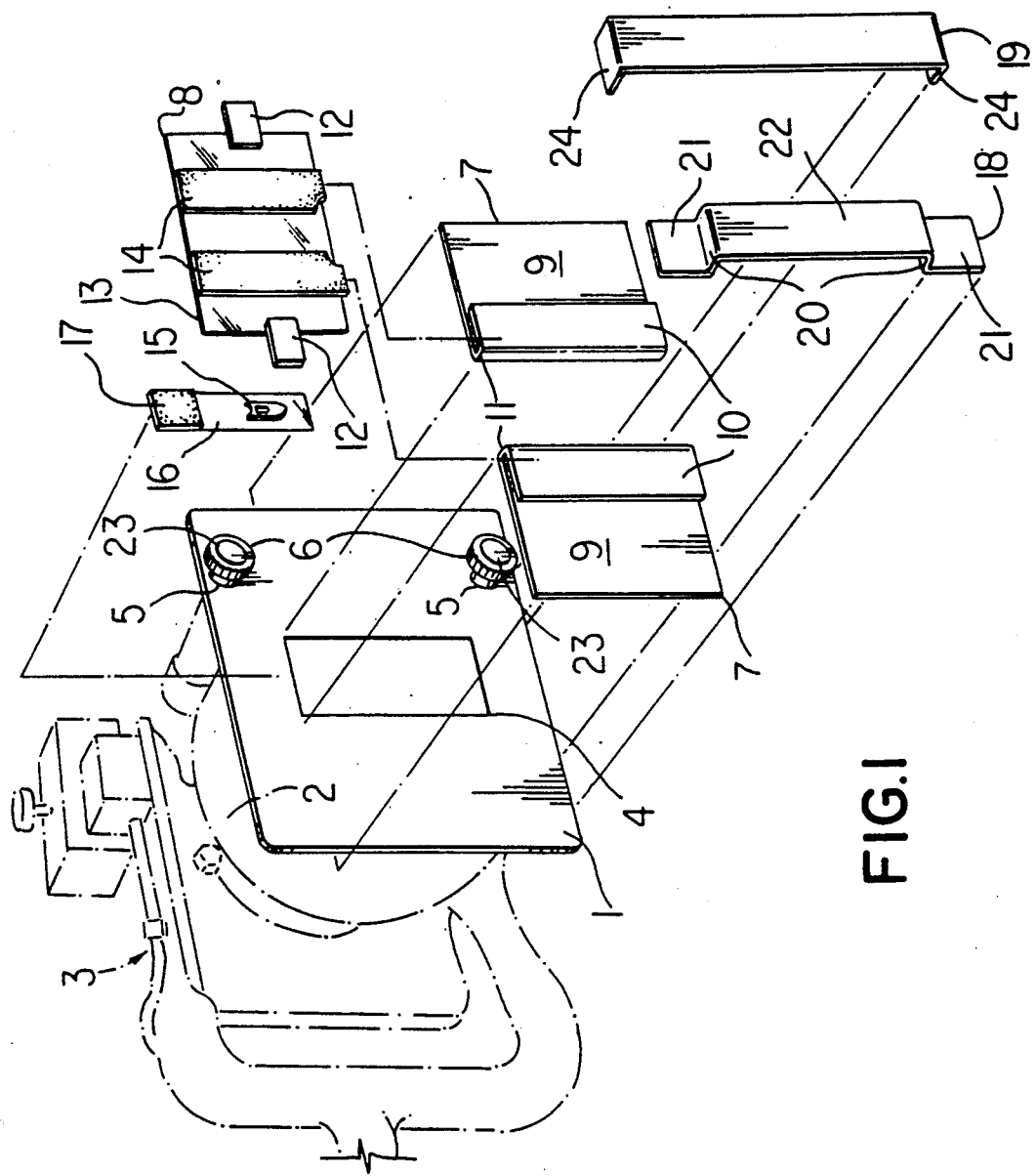
FIG. 1 is an exploded, perspective view of an X-ray shielding support device in accordance with the present invention.

With reference to the drawings, the X-ray shielding support device of the present invention includes a rectangular, metal, magnetic base plate 1 for mounting on the collimator 2 of an X-ray machine generally indicated at 3. A rectangular opening 4 is provided in the plate 1. The opening 4 is equal in area to the area of the collimator aperture when fully opened. Holes 5 for collimator aperture adjustment bolts (not shown) are provided in one side of the plate 1. The bolts are rotated by knobs 6 on the exterior of the plate 1.

A magnetic spacer 7 of generally J-shaped cross section is mounted on each side of the opening 4 for supporting one or more X-ray shield or filter holders 8 (FIGS. 1 and 2) spaced from the plate 1. Each spacer 7 includes a planar base 9 for mounting on the base plate 1, and an outer plate 10 connected to the base 9 by a web 11. The outer plate 10 is used to support a variety of filter holders such as the holders 8. Each holder 8 includes a magnetic arm or body 12 for connecting the holder to the plate 10, and a thin plastic sheet 13 carrying the arms 12 and a filter defined by lead plates 14.

Figure 2:
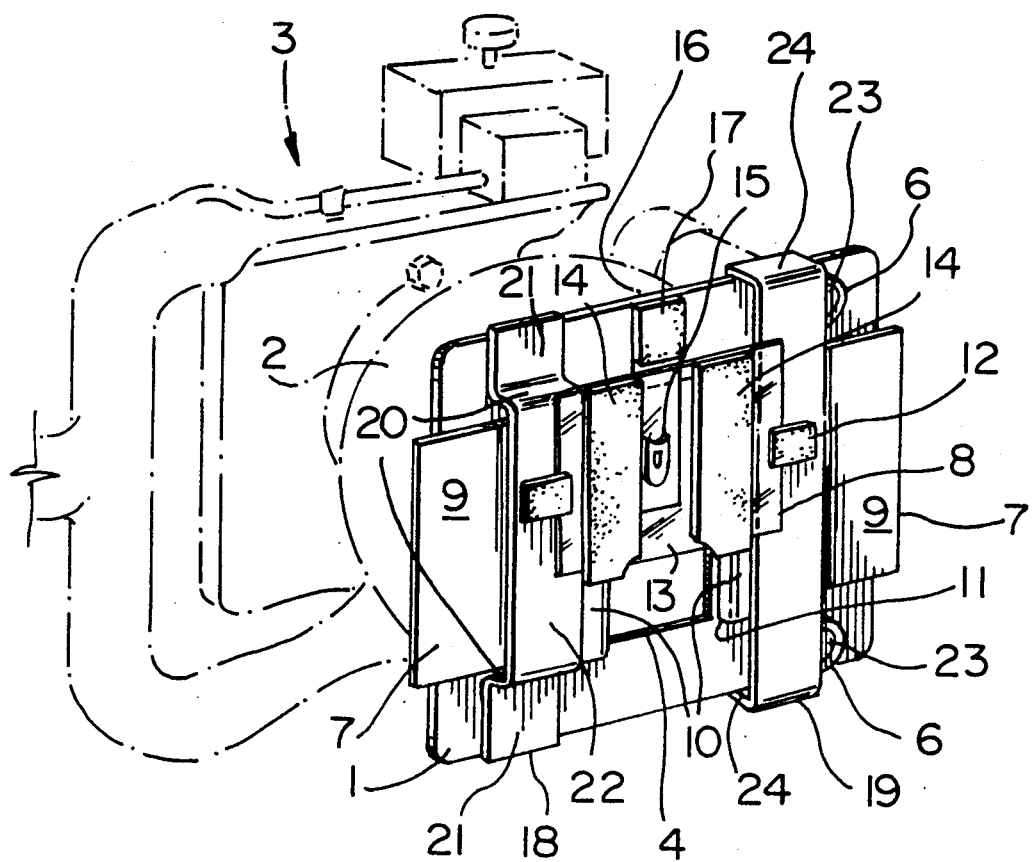
FIG. 2 is a perspective view of the device of FIG. 1 in the use condition.

As shown in FIGS. 1 and 2, a filter/holder combination can be mounted directly on the base plate 1. In this case, a smaller filter 15 is mounted on a plastic strip 16. The strip defines one end of an arm, the other end 17 of which is magnetic metal or metal coated for mounting on the plate 1 with the filter 15 in the path of the X-rays.

Additional spacers defined by magnetic metal strips or bars 18 and 19 (FIG. 1) are provided for mounting other filter elements (not shown) in front of the collimator aperture 4. The bar 18 is stepped, including shoulders 20 near each end. The ends 21 of the bar 18 are mounted directly on the plate 1 with the central portion 22 of the bar spaced from the base plate 1 by a distance greater than the plate 10. The other bar 19 is generally C-shaped for clearing the knobs 6. A magnetic disc 23 is provided on the outer end of each knob 6 for holding the bar 19 on the device. The ends 24 of the bar 19 maintain the strip in proper spaced apart relationship to the base plate.

Figure 3:
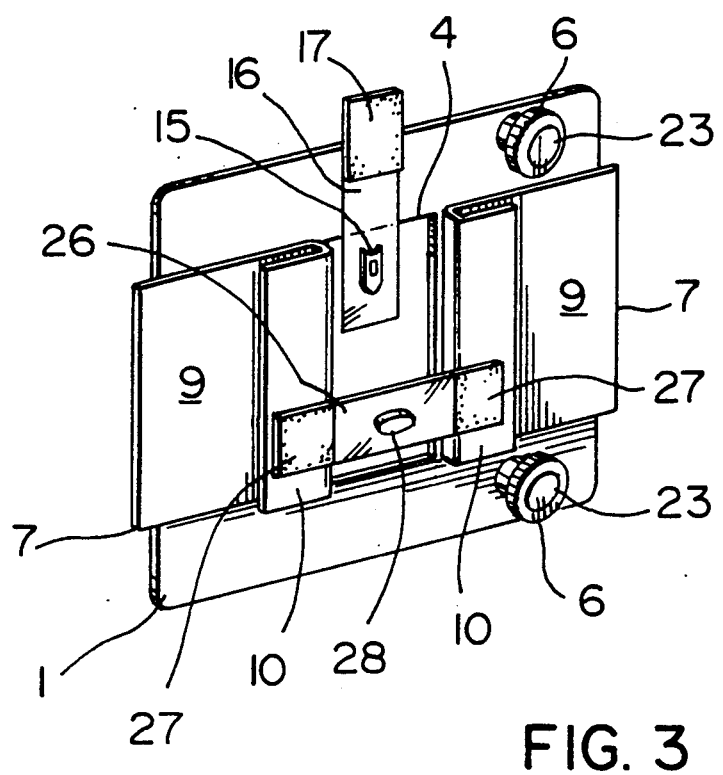
FIG. 3 is a perspective view of a device similar to that of FIG. 1 in the use position.
Figure 4:
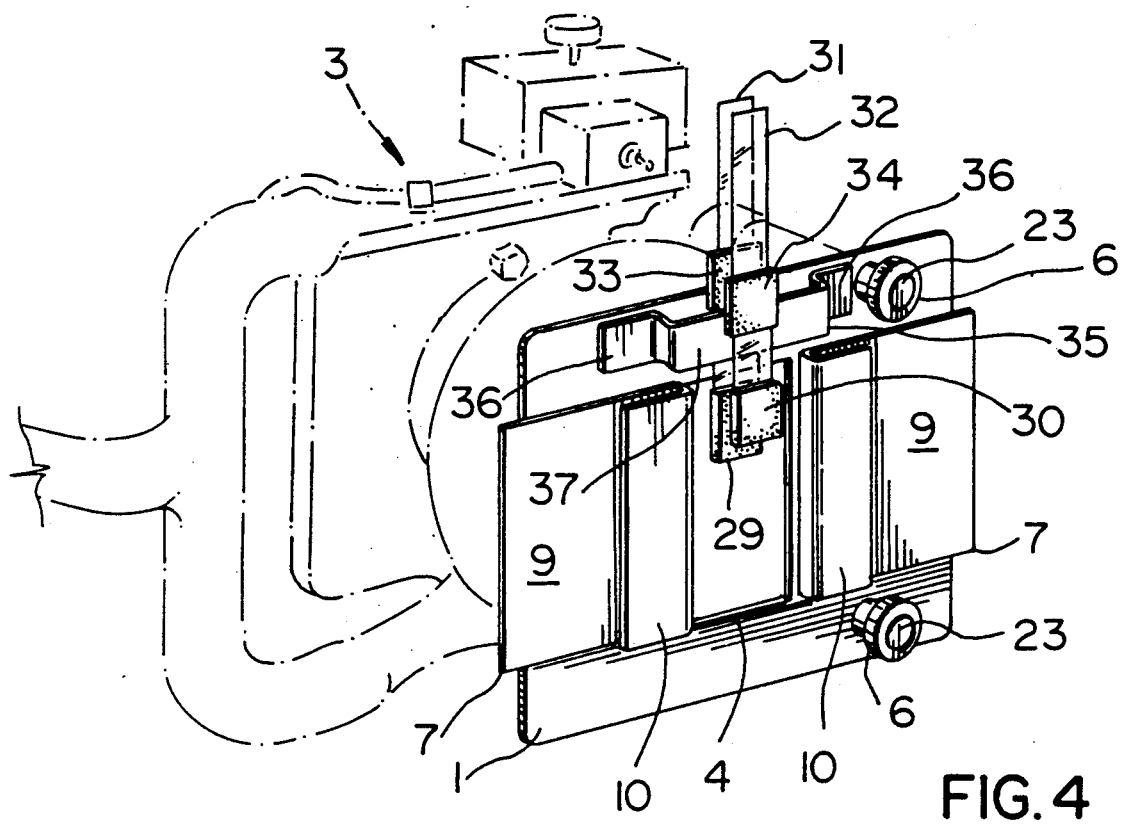
FIG. 4 is a perspective view of the basic elements of the device of FIG. 1 with an X-ray shield attached.

As shown in FIGS. 3 and 4, additional holders and filters or shields can be mounted on the base plate 1 or on the spacers 7. Referring to FIG. 3, a holder 25 for extending between the spacers 7 includes a transparent strip 26 with magnetic ends 27. A filter 28 is mounted in or on the strip 26. FIG. 4 illustrates the use of filters 29 and 30 in overlapping relationship to each other, and spaced from the collimator aperture. The filters 29 and 30 are mounted on one end of holders defined by transparent plastic strips 31 and 32, respectively. The strips 31 and 32 carry magnetic bodies 33 and 34, respectively for mounting the strips on the base plate 1 and a spacer bar 35, respectively. The bar 35 is similar to but shorter than the bar 18. As is the case with the bar 18, the ends 36 of the bar 35 are mounted directly on the base plate 1, and the center portion 37 supports the body 34 so that the filter holder is spaced from the collimator aperture a greater distance than the spacer plate 10.

In use, depending upon the area of the X-ray beam to be filtered or masked, one or more holders and filters are magnetically mounted directly on the base plate 1, or on one or more of the spacers 7, 18, 19 and 35. It will be appreciated that all or only some of the base plate 1, the spacers 7, 18, 19 and 35, and the metal portions of the filter holders are magnetic. It is merely necessary, that sufficient of the elements be magnetic that the remaining elements can be connected thereto.

The use of a base plate with a variety of spacers removably mountable thereon permits the X-ray machine operator to arrange individual or a plurality of filters at any position in the path of the X-ray beam. The filters can completely or partially overlap. Thus, a filter composite can be custom-built on the collimator using different sizes, shapes and thickness of filter components. The milti-level spacers permit independent movement in any direction to any position in the X-ray beam. Total compensation for a situation of a potentially extreme contrast can be accomplished by using a single filter or several layers of filters, each of which fills a specific need in a particular location in the X-ray beam.

I claim:

1. An X-ray shielding support device comprising apertured, metal base plate means for defining a frame around the collimator aperture of an X-ray machine; metal spacer means for mounting on said base plate means to define a support surface around and spaced from the collimator aperture and base plate means; and X-ray filter holder means for mounting on at least one of said base plate means and said spacer means, selective of said base plate means, spacers means and filter holder means being magnetic, whereby the holder means can be mounted on said base plate means or on said spacer means to shield any area in front of the collimator aperture.

2. A device according to claim 1, wherein said spacer means includes side plate means for mounting on at least one side base plate means, said side plate means having spaced apart arms for supporting filter holder means in spaced apart relationship to said base plate means and said collimator aperture.

3. A device according to claim 2, wherein said side plate means is generally J-shaped in cross section, including a planar inner arm for mounting on said base plate means, and a planar outer arm spaced from said inner arm for supporting filter holder means.

4. A device according to claim 1, wherein said spacer means includes elongated strip means having end portions for mounting on said base plate means and a central portion integral with said end portions for retaining a filter holder means spaced apart from said end portions and base plate means.

5. A device according to claim 1, wherein said filter holder means includes a transparent plastic strip; and at least one magnetic section in said strip for retaining the strip on said base plate means or on a spacer means.

6. A device according to claim 1, wherein said holder means includes a transparent plastic sheet for carrying a filter, and magnetic arm means connected to said sheet for retaining the holder means on said base plate means or on said spacer means.

* * * * *